United States Patent [19]

Simon et al.

[11] Patent Number: 5,776,472
[45] Date of Patent: Jul. 7, 1998

[54] UVA PHOTOPROTECTIVE COSMETIC/ DERMATOLOGICAL COMPOSITIONS COMPRISING IRON CHELATING AGENTS

[75] Inventors: Pascal Simon, Vitry Sur Seine; Didier Gagnebien, Chatillon, both of France

[73] Assignee: Societe L'Oreal S.A., Paris, France

[21] Appl. No.: 685,913

[22] Filed: Jul. 22, 1996

[30] Foreign Application Priority Data

Jul. 20, 1995 [FR] France .................. 95 08817

[51] Int. Cl.$^6$ .................. A61K 7/48
[52] U.S. Cl. .................. 424/401; 514/844; 514/846; 514/847; 514/938; 514/944
[58] Field of Search .................. 424/401; 514/844, 514/846, 847, 938, 944

[56] References Cited

U.S. PATENT DOCUMENTS

| 4,585,597 | 4/1986 | Lang et al. .................. 260/507 |
| 5,352,438 | 10/1994 | N'Guyen et al. .................. 424/45 |
| 5,487,884 | 1/1996 | Bisset et al. .................. 424/59 |

FOREIGN PATENT DOCUMENTS

| 0313305 | 4/1989 | European Pat. Off. . |
| 0671160 | 9/1995 | European Pat. Off. . |
| 91/04777 | 8/1992 | Netherlands . |
| 94/04128 | 3/1994 | WIPO . |
| 94/04131 | 3/1994 | WIPO . |

OTHER PUBLICATIONS

Database WPI, Week 8927, Derwent Publications Ltd., London, GB; AN 89–197258.

Patent Abstracts of Japan, vol. 11, No. 53 (C–404) [2500].

*Primary Examiner*—Jyothsan Venkat
*Attorney, Agent, or Firm*—Oblon, Spivak, McClelland, Maier,& Neustadt, P.C.

[57] ABSTRACT

Topically applicable UVA photoprotective cosmetic/ dermatological compositions comprise an effective photoprotecting amount of at least one UVA screening agent substituted by at least one optionally neutralized sulfo functional group, and an effective UVA photoprotecting-enhancing amount of at least one otherwise non-UVA photoprotecting iron chelating agent, thereby imparting a synergistic protection factor (PF) effect thereto, in a cosmetically/dermatologically acceptable topical vehicle, carrier or diluent therefor.

18 Claims, No Drawings

UVA PHOTOPROTECTIVE COSMETIC/DERMATOLOGICAL COMPOSITIONS COMPRISING IRON CHELATING AGENTS

BACKGROUND OF THE INVENTION

1. Technical field of the invention:

The present invention relates to a novel topically applicable cosmetic/dermatological compositions for the photoprotection of human skin and/or hair. The subject compositions prevent and/or to combat aging of the skin, especially due to ultraviolet A radiation, and protect the skin and/or the hair against such radiation and against free radicals. The compositions of the invention are formulated, for example, as smooth white creams or as gels which may be topically applied to the human face, body and/or legs and to the hands and scalp.

2. Description of the prior art:

It is known to this art that, over time, various signs which are very characteristic of aging appear on the skin, reflected in particular in a modification of the cutaneous structure and functions.

The principal clinical signs of cutaneous aging are, notably, the appearance of deep wrinkles and fine lines, which increase with age. In particular, disruption of the "grain" of the skin is observed, namely, its microrelief is less uniform and is anisotropic in nature.

Moreover, the skin complexion is generally modified; it appears paler and yellower, which appears to be due essentially to disruption of the microcirculation (less haemoglobin in the dermal papillae). Furthermore, many colored and/or darker blemishes appear on the skin surface, and more especially on the hands, imparting heterogeneity to the skin. In general, these blemishes are due to considerable production of melanin in the skin epidermis and/or dermis. In certain instances, these blemishes may become cancerous. Thus, it is increasingly sought to reduce these blemishes, or even to eliminate same. Too, diffuse irritations, and sometimes telangiectasia, may occur on certain areas of the skin.

Another clinical indication of aging is the dry and rough appearance of the skin, which is essentially due to a more considerable desquamation; by scattering light rays, these squama also contribute to the somewhat grey appearance of the complexion.

Finally, a loss of firmness and of tonicity of the skin is observed which, as in the case of wrinkles and fine lines, is at least partly explained by a dermal and epidermal atrophy and flattening out of the dermoepidermal formation; the skin is thinner and more flaccid, and the thickness of the epidermis decreases.

It is thus observed that the clinical signs of cutaneous aging result essentially from a dysfunction of the principal biological mechanisms taking place in the skin.

Such aging can be physiological in nature but also photoinduced, namely, due to repeated exposure of the skin to sunlight, and especially to ultraviolet A irradiation. The action of this light on the constituents of the skin and on the sebum secreted by the skin results, in particular, in the formation of oxygenated free radicals. These free radicals inflict considerable damage, especially in cell membranes (permeability of the membranes), cell nuclei (mutation by action on RNA or DNA) and tissues (necrosis and degeneration); it is thus necessary to protect the skin against these free radicals.

Hence, serious need continues to exist in this art for compositions capable of preventing and/or combating the onset of aging and the signs of aging, such as wrinkles and fine lines, of preventing and/or combating skin pigmentation blemishes, whatever their origin, and of protecting the skin, especially by suppression of the formation of oxygenated free radicals.

One of the known means for effectively combating premature aging of the skin is to topically apply thereto a UVA screening agent which absorbs at wavelengths between 320 and 400 nm. This decreases the excess photoinduced free radicals. However, such photoprotection is less than complete with the majority of compositions containing UVA screening agents. Thus, upon repeated exposures, the residual amount of free radicals, persisting despite the protection by the UVA screening agent, can induce, over the long term, photoactinic aging phenomena.

It has been proposed to increase the amounts of UVA screening agents, but it is not advisable to apply excessively large levels of screening agents in cosmetic products for daily care. Indeed, with the majority of screening agents, a maximum protection factor is often attained which is very difficult to improve by increasing the level of screening agents. In addition, it is necessary to take account of the fact that daily care products are more frequently used than other seasonal products containing screening agents, such as sunscreen products for example, which can result in cosmetic discomfort and problems of toxicity by the topical route.

In order to more effectively combat photoactinic aging, it is therefore advantageous to employ means other than the use of large amounts of UVA screening agent. In particular, it is possible to combine, with UVA screening agents, molecules capable of blocking the chain reactions of free radicals before the final stages of degradation of the biological constituents of the skin. These compounds are antioxidizing agents and/or anti-free radicals.

It too is known that photoinduced free radicals arise principally from molecular oxygen. Given that it is common in the body and that it is readily able to accept electrons, the free radicals and the activated oxygen species which derive therefrom are the most numerous participants in radical reactions. The following are representative:

Singlet oxygen: non-radical, high oxidizing, very toxic and very rare because it has a very short lifetime. It is the product of the excitation of molecular oxygen by light photons.

The superoxide radical anion: it is the product of the addition of an electron to molecular oxygen. It can initiate the production of very reactive free radicals, the hydroxyl radicals.

Hydrogen peroxide: non-radical but which can initiate the production of hydroxyl radicals.

The hydroxyl radical: it is highly oxidizing, and therefore very reactive, and the most toxic in respect of human cells.

Exemplary thereof are lipoperoxide radicals, which are species derived from the oxidation of membrane lipids.

Extracellular iron is also representative, which, by reacting with hydrogen peroxide and the superoxide radical anion which have accumulated outside the cell, will promote the production of the hydroxyl radical.

SUMMARY OF THE INVENTION

In order to effectively combat oxygenated free radicals and thus to combat photoaging, a unique combination of a UVA screening agent with one or more antioxidizing and/or antiradical molecules has now unexpectedly and surprisingly been developed which exhibits a synergistic effect and especially a protection factor greater than that of the screening agent alone, whereas these antioxidizing and/or antiradical molecules themselves exhibit no screening activity for UVA radiation.

Briefly, it has now surprisingly been found that, on combining one or more iron chelating agents with one or more UVA photoprotective agents, the screening power of the latter is increased.

DETAILED DESCRIPTION OF BEST MODE AND

SPECIFIC/PREFERRED EMBODIMENTS OF THE INVENTION

More particularly according to the present invention, provided are novel compositions for topical application, intended especially for preventing and/or combating aging of the skin and/or cutaneous blemishes and/or protecting the skin and/or the hair against ultraviolet radiation and/or against free radicals, which exhibit an effectiveness which is conspicuously greater than that of the prior art.

In a preferred embodiment of the invention, the subject compositions contain, in a medium (vehicle, carrier or diluent) acceptable for topical application, at least one screening agent which absorbs at least ultraviolet A irradiation, including at least one optionally neutralized sulfo functional group, and at least one iron chelator or chelating agent which does not exhibit the property of screening such radiation, the screening agent and the chelator being present in an amount such that they synergistically act to impart to the composition a protection factor in respect of ultraviolet A radiation which is greater than that of the screening agent alone.

The screening power of the subject compositions in the UVA range is represented by the protection factor, designated PF. The determination of the screening power UVA is based on the technique for evaluation of the pigmentation induced by UVA (Persistant Pigment Darkening : PPD). This technique is described by Chardon and al, Method for the UVA Protection assessment of sunscreens based on residual immediate pigment darkening, 20th Annual Meeting of the American Society for Photobiology, Marco island, Florida (USA), June 20–24, 1992.

The iron chelating agent or agents advantageously have an association constant with ferrous or ferric ions greater than $10^2$, preferably greater than $10^6$. Exemplary iron chelating agents include the salts of ethylenediaminetetramethylenephosphonic acid, and especially the pentasodium salts, and ethylenediaminetetraacetic acid. Also representative thereof are citric acid, tartaric acid, phytic acid and salts thereof and dibenzyldithiocarbamate. They are formulated in a proportion of 0.001% to 5% and preferably of 0.1% to 2% of the total weight of the composition.

The compositions of the invention preferably contain one or more other antioxidizing and/or antiradical agents selected from among agents for combating lipoperoxide radicals, compounds for regenerating oxidized vitamin E, agents for combating the hydroxyl radical, agents for combating singlet oxygen and agents for combating the superoxide radical anion, and combinations thereof. These compounds are addvantageously present in amounts ranging from 0.0001% to 5%.

The compositions of the invention contain one or more UVA screening or photoprotecting agents in an amount which is effective for screening such UVA radiation. In actual practice, these screening agents typically constitute from 0.01% to 10%, preferably from 0.1% to 5%, of the total weight of the composition. These screening agents are molecules containing one or more optionally neutralized sulfo functional groups or molecules containing one or more sulfonate functional groups.

The bases used to neutralize one or more sulfo functional groups of the UVA screening agents are preferably organic bases, generally used in the cosmetics field, such as triethanolamine and ethylenediamine.

The UVA screening agents which may be used in the invention may be lipophilic or, preferably, hydrophilic. Exemplary such screening agents include sulfo or sulfonate derivatives of benzophenone, such as 2-hydroxy-4-methoxybenzophenone-5-sulfonic acid, marketed by BASF under the trademark Uvinul MS-40, and sulfo or sulfonate derivatives of benzylidenecamphor.

In particular, the benzylidenecamphor derivatives which may be formulated into the compositions of the invention have the following general formula (a):

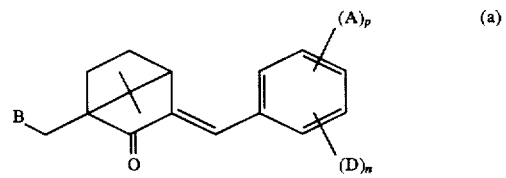

in which B represents -H or -SO$_3$H; $0 \leq p \leq 1$ wherein B=-SO$_3$H when p=0; $0 \leq n \leq 4$; D represents one or more linear or branched chain alkyl or alkoxy radicals, which may be identical or different when $n \leq 2$, having from about 1 to 18 carbon atoms, a halo atom or a hydroxyl radical; A, preferably in the meta or para position, represents either an -SO$_3$H radical, or a radical:

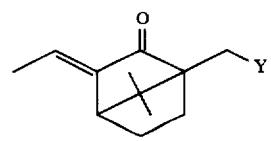

in which Y represents -H or -SO$_3$H, or a radical:

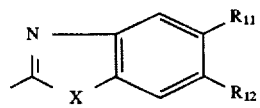

in which R$_{11}$ is a hydrogen atom, a linear or branched chain alkyl or alkoxy radical having from about 1 to 6 carbon atoms or the -SO$_3$H radical, R$_{11}$ being -SO$_3$H when B=-H; R$_{12}$ is a hydrogen atom or a linear or branched chain alkyl or alkoxy radical having from about 1 to 6 carbon atoms; X is an oxygen or sulfur atom or a radical -NR-, wherein R is a hydrogen atom or a linear or branched chain alkyl radical having from about 1 to 6 carbon atoms, and in which at least one -SO$_3$H functional group is optionally neutralized.

Specific examples of compounds of formula (a) which are representative of the compounds of formulae (I), (II) and (III) are set forth below: Formula (I):

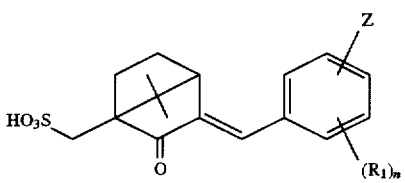

in which Z, preferably in the para or meta position, is a radical:

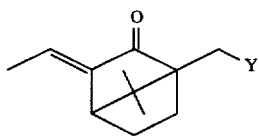

wherein Y is -H or -SO$_3$H, which is optionally neutralized; n is equal to 0 or is a number ranging from 1 to 4 (0≦n≦4); and R$_1$ is one or more linear or branched chain alkyl or alkoxy radicals, which may be identical or different, having from about 1 to 4 carbon atoms.

A particularly preferred compound of formula (I) is that corresponding to n=0, Z in the para position and Y=-SO$_3$H: benzene-1,4-[di(3-methylidene-10-camphorsulfonic)] acid which is also referred to (according to CTFA nomenclature, 5th Edition) as terephthalylidenedicamphorsulfonic acid. Formula (II):

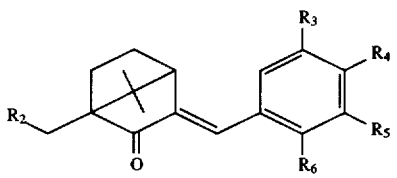

in which R$_2$ is a hydrogen atom or an -SO$_3$H radical; R$_3$, R$_4$, R$_5$ and R$_6$, which may be identical or different, are each a hydroxyl group, a linear or branched chain alkyl radical having from about 1 to 4 carbon atoms, a linear or branched chain alkenyl radical having from 2 to 4 carbon atoms, a linear or branched chain alkoxy radical having from 1 to 4 carbon atoms, a linear or branched chain alkenyloxy radical having from 2 to 4 carbon atoms, or a halo atom; furthermore, only one radical R$_3$ to R$_6$ may be an -SO$_3$H radical, at least one of the radicals R$_3$ to R$_6$ denoting the -SO$_3$H radical when R$_2$ is a hydrogen atom. One or more -SO$_3$H functional groups may also be neutralized.

Specific examples which are representative are the following compounds of formula (II), in which:

R$_4$ is the -SO$_3$H radical in the para position of benzylidenecamphor and R$_2$, R$_3$, R$_5$ and R$_6$ are each a hydrogen atom, i.e., 4'-sulfo-3-benzylidenecamphor;

R$_3$, R$_4$, R$_5$ and R$_6$ are each a hydrogen atom and R$_2$ is an -SO$_3$H radical, i.e., 3-benzylidene-10-camphorsulfonic acid;

R$_4$ is a methyl radical in the para-position of benzylidenecamphor, R$_5$ is an -SO$_3$H radical and R$_2$, R$_3$ and R$_6$ are each a hydrogen atom, i.e., 4'-methyl-3'-sulfo-3-benzylidenecamphor;

R$_4$ is a chlorine atom in the para-position of benzylidenecamphor, R$_5$ is an -SO$_3$H radical and R$_2$, R$_3$ and R$_6$ are each a hydrogen atom, i.e., 4'-chloro-3'-sulfo-3-benzylidenecamphor;

R$_4$ is a methyl radical in the para-position of benzylidenecamphor, R$_3$, R$_5$ and R$_6$ are each a hydrogen atom and R$_2$ is an -SO$_3$H radical, i.e., 4'-methyl-3-benzylidene-10-camphorsulfonic acid;

R$_2$ is an -SO$_3$H radical, R$_3$ is a methyl radical, R$_4$ is a hydrogen atom, R$_5$ is a tert-butyl radical and R$_6$ is a hydroxyl radical, namely, 3'-t-butyl-2'-hydroxy-5'-methyl-3-benzylidene-10-camphorsulfonic acid;

R$_2$ is an -SO$_3$H radical, R$_3$ is a methoxy radical, R$_4$ is a hydrogen atom, R$_5$ is a tert-butyl radical and R$_6$ is a hydroxyl radical, i.e., 3'-t-butyl-2'-hydroxy-5'-methoxy-3-benzylidene)-10-camphorsulfonic acid;

R$_2$ is an -SO$_3$H radical, R$_3$ and R$_5$ are each a tert-butyl radical, R$_4$ is a hydroxyl radical and R$_6$ is a hydrogen atom, i.e., 3',5'-di-tert-butyl-4'-hydroxy-3-benzylidene-10-camphorsulfonic acid;

R$_4$ is a para-methoxy radical, R$_5$ is -SO$_3$H and the radicals R$_2$, R$_3$ and R$_6$ are each H, namely, 4'-methoxy-3'-sulfo-3-benzylidenecamphor;

R$_2$ is an -SO$_3$H radical, R$_3$ and R$_6$ are each H or R$_4$ and R$_5$ together form a methylenedioxy radical, i.e., 3',4'-methylenedioxy-3-benzylidene-10-camphorsulphonic acid;

R$_2$ is an -SO$_3$H radical, R$_4$ represents a methoxy radical and the radicals R$_3$, R$_5$ and R$_6$ represent H, namely, 4'-methoxy-3-benzylidene-10-camphorsulfonic acid;

R$_2$ represents an -SO$_3$H radical, R$_4$ and R$_5$ are each a methoxy radical and the radicals R$_3$ and R$_6$ are each H, namely, 3',4'-dimethoxy-3-benzylidene-10-camphorsulfonic acid;

R$_2$ is an -SO$_3$H radical, R$_4$ is an n-butoxy radical and the radicals R$_3$, R$_5$ and R$_6$ are each a hydrogen atom, i.e., 4'-n-butoxy-3-benzylidene-10-camphorsulfonic acid;

R$_2$ is an -SO$_3$H radical, R$_4$ is an n-butoxy radical, R$_5$ is a methoxy radical and R$_3$ and R$_6$ are each a hydrogen atom, i.e., 4'-n-butoxy-3'-methoxy-3-benzylidene-10-camphorsulfonic acid. Formula (III):

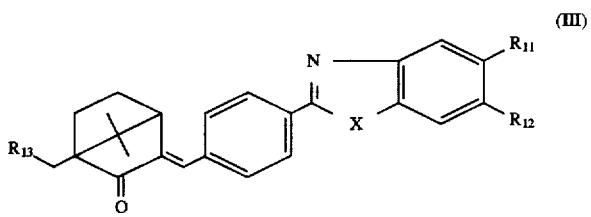

in which R$_{11}$, is a hydrogen atom, a linear or branched chain alkyl or alkoxy radical having from about 1 to 6 carbon atoms, or an -SO$_3$H radical, R$_{12}$ is a hydrogen atom or a linear or branched chain alkyl or alkoxy radical having from about 1 to 6 carbon atoms, R$_{13}$ is a hydrogen atom or an -SO$_3$H radical, with the proviso that at least one of the radicals R$_{11}$ and R$_{13}$ is an -SO$_3$H radical, and X is an oxygen or sulfur atom or a group -NR-, wherein R is a hydrogen atom or a linear or branched chain alkyl radical having from about 1 to 6 carbon atoms.

One specific example of a compound of formula (III) which is particularly representative is the compound in which X is an -NH- radical, R$_{11}$ is an -SO$_3$H radical, and R$_{12}$ and R$_{13}$ are each a hydrogen atom, i.e., 2-[4-(camphormethylidene)phenyl]benzimidazole-5-sulfonic acid.

The compounds of structural formulae (I), (II) and (III) are described in U.S. Pat. No. 4,585,597 and in FR-2.236, 515, 2,282,426, 2,645,148, 2,430,938 and 2,592,380.

Other benzylidenecamphor compounds of the invention include the compounds of general formula (b):

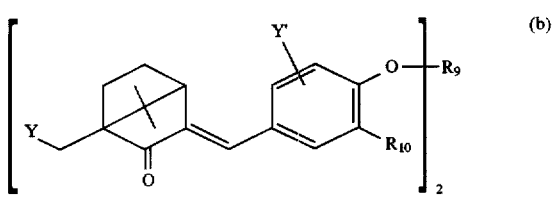

(b)

in which $R_9$ is a divalent radical -$(CH_2)_m$- or -$CH_2$-CHOH-$CH_2$-, wherein $\underline{m}$ is an integer ranging from 1 to 10 ($1 \leq \underline{m} \leq 10$); $R_{10}$ is a hydrogen atom, an alkoxy radical having from about 1 to 4 carbon atoms, or a divalent radical -O- bonded to the radical $R_9$ when the latter is also divalent; and Y and Y' are each a hydrogen atom or an -$SO_3H$ radical, at least one of these radicals Y or Y' being other than hydrogen. In this instance also, the -$SO_3H$ functional group may be neutralized.

One specific example of a compound of formula (b) is that in which Y is -$SO_3H$, Y' is -H, $R_{10}$ is H and $R_9$ is -$CH_2$-$CH_2$-, i.e., ethylenebis|3-(4'-oxybenzylidene)-10-camphorsulfonic| acid.

It is possible to use one or more active agents for combating lipoperoxide radicals in an amount preferably ranging from 0.05% to 5% and, preferably, from 0.2% to 3% of the total weight of the composition. These agents include, for example, vitamin E (or D,L-α-tocopherol) and derivatives thereof, or any other compound which is effective in vitro in the so-called β-carotene test or in the rancimat test, such as γ-orizanol, natural extracts, such as the OPCs of hawthorn, of pine or of grape, or extracts of gall apple or of rosemary.

The compositions of the invention advantageously contain at least one UVA screening agent, such as benzene-1,4-[di(3-methylidene-10-camphorsulfonic)] acid, one iron chelator, such as Dequest 2046, and one agent for combating lipoperoxide radicals, for example vitamin E.

The compositions of the invention may be formulated into all pharmaceutical dosage forms normally employed for topical application, such as solutions, aqueous or aqueous/alcoholic gels, oil-in-water or water-in-oil emulsions, and more particularly droplets of oil dispersed by means of spherules in an aqueous phase. These spherules may be polymeric nanoparticles such as nanospheres and nanocapsules or, preferably, may be lipid vesicles. The compositions of the invention may be provided in the form of a cream, an ointment, a gel, a lotion or a serum.

The oils which may be included according to the invention are those generally employed in the cosmetics/sunscreen arts. They may be plant, mineral or synthetic oils, and may optionally be silicone-containing and/or fluorinated oils.

The compositions of the invention may also contain hydrophilic or lipophilic adjuvants and additives such as gelling agents, preservatives, opacifying agents, emulsifying agents, co-emulsifying agents, neutralizing agents, fragrances and dissolving agents or peptizing agents thereof, colorants such as dyes and pigments, and fillers, as well as lipophilic or hydrophilic active agents other than iron chelators and chemical screening agents which absorb in the ultraviolet A. In particular, it is possible to add UVB screening agents to the subject compositions, for the purpose of preventing sunburn and sunstroke upon exposure to sunlight.

The amounts of oil and of water are generally those coventional in this art and depend on the pharmaceutical dosage form of the composition. For an oil-in-water emulsion or a dispersion of oil in water by means of lipid spherules, the oil may constitute from 0.5% to 60%, preferably from 2% to 40%, of the total weight of the composition.

Similarly, the adjuvants and additives are formulated in the usual amounts and may constitute, in total, from 0.1% to 20% by weight. The amount of adjuvants and additives depends on their nature.

The compositions of the invention may be applied topically to all regions of the body and of the face, including the scalp, the legs and the hands.

The present invention also features the use of the subject compositions for the cosmetic treatment of wrinkles and/or fine lines of the skin, induced via UVA irradiation, as well as for protecting, moisturizing and/or firming the skin.

Too, this invention features the use of the subject compositions for combating photoinduced skin aging.

This invention also relates to the use of the subject compositions for depigmenting the skin and/or cosmetically treating skin blemishes attributed to aging, these blemishes afflicting the face and/or the body, including the hands and the scalp, as well as for formulation into a cream suitable for the treatment of skin blemishes of pathological origin.

The subject compositions are also useful for protecting the skin against free radicals.

Thus, the present invention features the cosmetic and/or dermatological treatment of the skin, comprising topically applying the subject compositions thereto.

In order to further illustrate the present invention and the advantages thereof, the following specific examples are given, it being understood that same are intended only as illustrative and in nowise limitative. In said examples to follow, the constituents of the compositions are expressed in % by weight.

EXAMPLE 1:

Tests were carried out to demonstrate the advantages of the present invention. The objective of the tests was to evidence the ability of the compositions of the invention to protect against free radicals.

The following composition (A) was prepared, by way of example: an oil-in-water emulsion containing a pentasodium salt of ethylenediaminetetramethylene-phosphonic acid (Dequest 2046 marketed by Monsanto) and benzene-1,4-[di (3-methylidene-10-camphorsulfonic)] acid. The composition (B), which was the same emulsion as the composition (A), but which contained only the UVA screening agent, was also prepared.

Surprisingly, the UVA protection factor (PF) of the composition (A) was greater than that of the screening agent alone, which indicates that the composition of the invention screened UVA radiation more efficiently than the screening agent alone.

The values of the UVA protection factors of the compositions (A) and (B) were measured in vivo on 5 test subjects (PPD method).

The results were: Composition (A)>Composition (B) for 80% of the subjects (15% increase).

The photoprotection in the UVA range of the composition (A) was therefore notably greater than that of the composition (B) containing the screening agent alone.

The following Examples 2–5 set forth specific embodiments of compositions according to the invention:

EXAMPLE 2: Water-in-oil cream for daily use on wrinkles: Composition:

| | | | |
|---|---|---|---|
| A₁: | (i) | Stearic acid | 0.4% |
| | (ii) | Polyethylene glycol stearate (40 EO) (emulsifying agent) | 3.5% |
| | (iii) | Glyceryl mono,di, tripalmitostearate (emulsifying agent) | 3.0% |
| | (iv) | Isopropyl palmitate (oil) | 7.0% |
| | (v) | Hydrogenated isoparaffin (6–8 mol of isobutylene) (oil) | 6.5% |
| A₂: | (vi) | Cyclopentadimethylsiloxane (oil) | 5.0% |
| B: | (vii) | Sterilized demineralized water q.s. | for 100% |
| | (viii) | Glycerol (moisturizing agent) | 3.0% |
| | (ix) | Iron chelating agent | 2.0% |
| | (x) | Denatured absolute ethyl alcohol | 10.0% |
| | (xi) | Methyl para-hydroxybenzoate (preservative) | 0.2% |
| C: | (xii) | Terephthalylidenedicamforsulfonic acid at a concentration of 33% in water | 3.3% |
| | (xiii) | Triethanolamine (neutralizing agent) | 0.7% |

Preparation of the phase $A_1+A_2$:

The constituents of $A_1$. were dissolved at 80° C. When the mixture was clear, the temperature was decreased to 65° C. and $A_2$ was added. The mixture was continuously clear and homogeneous. The temperature was maintained at 65° C. Formulation:

The constituents of B were dissolved at 85° C.–90° C. in a beaker. After assuring the clarity, the temperature was adjusted to 65° C. The emulsion was produced, with stirring, by pouring $(A_1+A_2)$ into B. The cooling was continued with stirring. At 40° C., phase C was added, again under stirring, and the mixture was permitted to cool to 20° C. with stirring.

A white care cream was obtained for protecting the skin, on a daily basis, from the deleterious effects of UV irradiation.

EXAMPLE 3: Gel for daily use and for protecting against sunlight: Composition:

| | | | |
|---|---|---|---|
| A: | (i) | Demineralized water | q.s. for 100% |
| | (ii) | Glycerol | 3.0% |
| | (iii) | Methyl para-hydroxybenzoate | 0.2% |
| | (iv) | Dequest 2046 | 1.0% |
| | (v) | Xanthan gum (thickening agent) | 0.2% |
| B: | (vi) | Parsol MCX (UVB screening agent) | 4.0% |
| | (vii) | Alkyl benzoate (Finsov TN marketed by Witco) | 4.0% |
| | (viii) | Carbomer (Pemulen TR 2, marketed by Goodrich) | 0.5% |
| | (ix) | Triethanolamine | 0.5% |
| C: | (x) | Terephthalylidenedicamphorsulfonic acid at a concentration of 33% in water | 2.3% |
| | (xi) | Triethanolamine (neutralizing agent) | 0.75% |

Formulation:

Phase A was prepared by sprinkling the gelling agent, with stirring, into the water containing the dissolved ingredients. Emulsification was carried out, phase B being incorporated into phase A, with stirring. The mixture was rendered smooth and was permitted to cool with slow paddle-stirring. Phase C was added at 35° C. and the mixture was permitted to cool to 25° C. with stirring.

EXAMPLE 4: Water-in-oil cream: Composition:

| | | | |
|---|---|---|---|
| A: | (i) | Protegin X (emulsifying agent) | 15.00% |
| | (ii) | Liquid petrolatum | 4.00% |
| | (iii) | Sunflower oil | 6.00% |
| B: | (iv) | Water | q.s. for 100% |
| | (v) | Glycerol | 5.00% |
| | (vi) | Iron chelating agent | 2.00% |
| | (vii) | Sodium chloride | 1.3% |
| C: | (viii) | Terephthalylidenedicamphorsulfonic acid at a concentration of 33% in water | 6.1% |
| | (ix) | Triethanolamine (neutralizing agent) | 1.2% |

EXAMPLE 5: Oil-in-water cream: Composition:

| | | | |
|---|---|---|---|
| A: | (i) | Methylglucose stearate (Glucate SS, Amerchol) | 3.00% |
| | (ii) | Stearic acid | 0.7% |
| | (iii) | Liquid petrolatum | 5.00% |
| | (iv) | Isostearyl isostearate | 5.00% |
| | (v) | Cyclomethicone | 5.00% |
| B: | (vi) | Sucrose stearate | 1.3% |
| | (vii) | Glycerol | 2.00% |
| | (viii) | Hexylene glycol | 4.00% |
| | (ix) | Water | q.s. for 100% |
| | (x) | Dequest 2046 (Iron chelating agent) | 2.00% |
| C: | (xi) | Terephthalylidenedicamphorsulfonic acid at a concentration of 33% in water | 2.5% |
| | (xii) | Triethanolamine (neutralizing agent) | 0.5% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable UVA photoprotective cosmetic/dermatological composition, comprising:
    an effective photoprotecting amount of at least one UVA benzylidene camphor compound selected from the group consisting of:
    (i) a compound of formula (II)

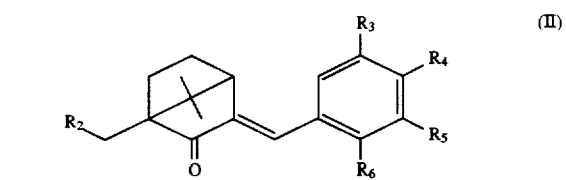

wherein $R_2$ is hydrogen or $-SO_3H$; $R_3$, $R_4$, $R_5$ and $R_6$, which may be identical or different, are each hydroxy, linear or branched chain alkyl having from 1–4 carbon atoms, linear or branched chain alkenyl having from 2–4 carbon atoms, linear or branched chain alkoxy having from 1–4 carbon atoms, linear or branched chain alkenyloxy having from 2–4 carbon atoms or halo, with the proviso that only one radical of the group $R_3$–$R_6$ may be -$SO_3H$ and that at least one of the radicals $R_3$–$R_6$ denote the -$SO_3H$ radical when $R_2$ is hydrogen;

(ii) a compound of formula (III):

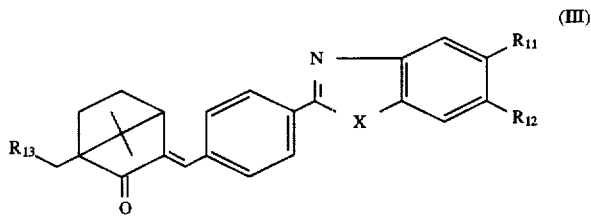

(III)

wherein $R_{11}$ is hydrogen, a linear or branched chain alkyl or alkoxy radical having from 1–6 carbon atoms, or -$SO_3H$; $R_{12}$ is hydrogen or a linear or branched chain alkyl or alkoxy group having from 1–6 carbon atoms; $R_{13}$ is hydrogen or -$SO_3H$, with the proviso that at least one of the radicals $R_{11}$ and $R_{13}$ is a -$SO_3H$ radical; and X is oxygen or sulfur or -NR-, wherein R is hydrogen or a linear or branched chain alkyl having from 1–6 carbon atoms; and (iii) a compound of formula (b):

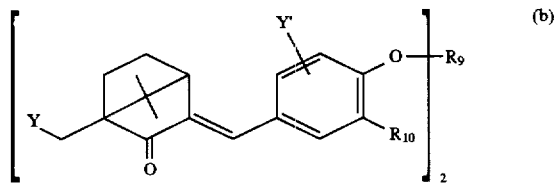

(b)

wherein $R_9$ is a divalent radical -$(CH_2)_m$- or -$CH_2$-CHOH-$CH_2$-, wherein m is an integer ranging from 1–10 ($1 \leq \underline{m} \leq 10$); $R_{10}$ is hydrogen, alkoxy having from 1–4 carbon atoms, or a divalent radical -O- bonded to radical $R_9$ when the latter is also divalent; and Y and Y' are each hydrogen or -$SO_3H$, at least one of Y or Y' being other than hydrogen, and an effective UVA photoprotecting-enhancing amount of at least one otherwise non-UVA photoprotecting iron chelating agent having an association constant with ferrous or ferric ions greater than $10^2$ and selected from the group consisting of dibenzyldithiocarbamate ethylenediaminetetramethylenephosphonic acid, ethylenediaminetetraacetic acid, citric acid, tartaric acid, phytic acid salts thereof and in a cosmetically/dermatologically acceptable topical vehicle, carrier or diluent therefor.

2. The cosmetic/dermatological composition as defined by claim 1, said association constant being greater than $10^6$.

3. The cosmetic/dermatological composition as defined by claim 1, said at least one iron chelating agent comprising a salt of ethylenediaminetetramethylenephosphonic acid.

4. The cosmetic/dermatological composition as defined by claim 1, said at least one iron chelating agent comprising from 0.001% to 5% by weight thereof.

5. The cosmetic/dermatological composition as defined by claim 4, said at least one iron chelating agent comprising from 0.1% to 2% by weight thereof.

6. The cosmetic/dermatological composition as defined by claim 1, said at least one UVA screening agent comprising from 0.01% to 10% by weight thereof.

7. The cosmetic/dermatological composition as defined by claim 6, said at least one UVA screening agent comprising from 0.1% to 5% by weight thereof.

8. The cosmetic/dermatological composition as defined by claim 1, comprising an emulsion, a gel, a cream, a lotion, an ointment, a serum, or a dispersion of spherules.

9. The cosmetic/dermatological composition as defined by claim 1, further comprising at least one antioxidant, anti-free radical agent, or combinations thereof.

10. The cosmetic/dermatological composition as defined by claim 9, wherein said at least one antioxidant, anti-free radical agent or combination thereof is a member selected from the group consisting of an agent for combating lipoperoxide radicals, a compound for regenerating oxidized vitamin E, an agent for combating hydroxyl radicals, an agent for combating singlet oxygen, an agent for combating superoxide radical anions, and combinations thereof.

11. The cosmetic/dermatological composition as defined by claim 1, comprising from 0.05% to 5% by weight of an agent for combating lipoperoxide radicals.

12. The cosmetic/dermatological composition as defined by claim 1, comprising from 0.02% to 3% by weight of an agent for combating lipoperoxide radicals.

13. The cosmetic/dermatological composition as defined by claim 1, comprising a pentasodium salt of ethylenediaminetetramethylenephosphonic acid and benzene-1,4-[di(3-methylidene-10-camphorsulfonic)] acid.

14. A treatment for protecting human skin, hair or combination thereof against the deleterious effects of UVA irradiation, comprising topically applying thereto an effective amount of the cosmetic/dermatological composition as defined by claim 1.

15. A treatment for protecting human skin, hair or combination thereof against the deleterious effects of free radicals, comprising topically applying thereto an effective amount of the cosmetic/dermatological composition as defined by claim 1.

16. A treatment for protecting human skin, hair or combination thereof against photoinduced aging, comprising topically applying thereto an effective amount of the cosmetic/dermatological composition as defined by claim 1.

17. A treatment for protecting human skin against wrinkles, fine lines, or both, comprising topically applying thereto an effective amount of the cosmetic/dermatological composition as defined by claim 1.

18. The cosmetic/dermatological composition as defined by claim 1, wherein the sulfonic acid group of the said at least one UVA screening agent is neutralized.

* * * * *